United States Patent
Okinishi

[11] Patent Number: 5,446,509
[45] Date of Patent: Aug. 29, 1995

[54] EYE FUNDUS PHOTOGRAPHING APPARATUS AND EYE FUNDUS CAMERA FOR CHANGING MAGNIFICATION WITH WHICH AN OBJECT IS PHOTOGRAPHED

[75] Inventor: Satoru Okinishi, Kawasaki, Japan
[73] Assignee: Canon Kabushiki Kaisha, Tokyo, Japan
[21] Appl. No.: 115,058
[22] Filed: Sep. 2, 1993
[30] Foreign Application Priority Data
    Sep. 3, 1992 [JP] Japan .................. 4-260750
[51] Int. Cl.⁶ .......................... A61B 3/12; A61B 3/14
[52] U.S. Cl. ........................... 351/206; 351/214; 351/221; 354/62
[58] Field of Search ............. 354/62; 351/207, 214, 351/205, 206, 221; 359/738, 739

[56]    References Cited
    U.S. PATENT DOCUMENTS

| | | | |
|---|---|---|---|
| 4,235,540 | 11/1980 | Hanamura et al. | 351/206 X |
| 4,265,518 | 5/1981 | Matsumura | 351/206 |
| 4,436,388 | 3/1984 | Takahashi et al. | 354/62 X |
| 4,558,932 | 12/1985 | Nunokawa | 351/206 |
| 4,679,919 | 7/1987 | Itoh et al. | 351/206 |
| 4,799,783 | 1/1989 | Takahashi et al. | 351/206 |

FOREIGN PATENT DOCUMENTS
63-36251 2/1988 Japan.

Primary Examiner—William L. Sikes
Assistant Examiner—David R. Parsons
Attorney, Agent, or Firm—Fitzpatrick, Cella, Harper & Scinto

[57] ABSTRACT

This invention relates to an eye fundus photographing apparatus for photographing the fundus of an eye to be examined. The eye fundus photographing apparatus has an optical system for illuminating the fundus of the eye to be examined and also causing the illuminated fundus of the eye to be examined to be photographed at different photographing magnifications. Also provided is an operating mechanism for changing the photographing magnification. The photographing magnification is changed by the operating mechanism being operated in a predetermined manner. In addition, an interlocking device is provided for varying a portion of the optical system without changing the photographing magnification, by the operation of the operating mechanism succeeding to the operation of the operating mechanism for changing the photographing magnification by the optical system.

11 Claims, 8 Drawing Sheets

EYE FUNDUS PHOTOGRAPHING APPARATUS AND EYE FUNDUS CAMERA FOR CHANGING MAGNIFICATION WITH WHICH AN OBJECT IS PHOTOGRAPHED

BACKGROUND OF THE INVENTION

1. Field of the Invention

This invention relates to an eye fundus photographing apparatus for photographing the fundus of an eye to be examined.

2. Related Background Art

Usually, when photographing the fundus of an eye to be examined having a small pupil diameter, it is more advantageous to photograph at a narrow field angle of a high magnification than to photograph at a wide field angle of a low magnification. However, when photographing at a narrow angle of field, as compared with the photographing at a wide angle of field, the quantity of photographing light is reduced and therefore, in Japanese Patent Publication No. 63-36251, a baffle comprising a circular light intercepting plate is installed in an illuminating optical system with a view to prevent the harmful effects of reflected light from the front face of the cornea or the rear face of the crystalline lens, and as the field angle is made narrower, the diameter of the baffle is made smaller so as to increase the quantity of photographing light.

However, in the above-described example of the prior art, when photographing an eye to be examined having a small pupil diameter, it is required to make the baffle and the diameter of an illuminating field stop smaller than in the ordinary case and therefore, a special condition must be set and a new operation must be added.

SUMMARY OF THE INVENTION

It is a first object of the present invention to provide an inexpensive eye fundus photographing apparatus which is excellent in operability when photographing is effected with a new function added.

It is a second object of the present invention to provide an inexpensive eye fundus photographing apparatus which eliminates the trouble to change over the field angle when photographing an eye to be examined having a small pupil diameter and is thus excellent in operability.

Other objects of the present invention will become apparent from the following detailed description of some embodiments of the invention.

DESCRIPTION OF THE PREFERRED EMBODIMENTS

Figure 1:
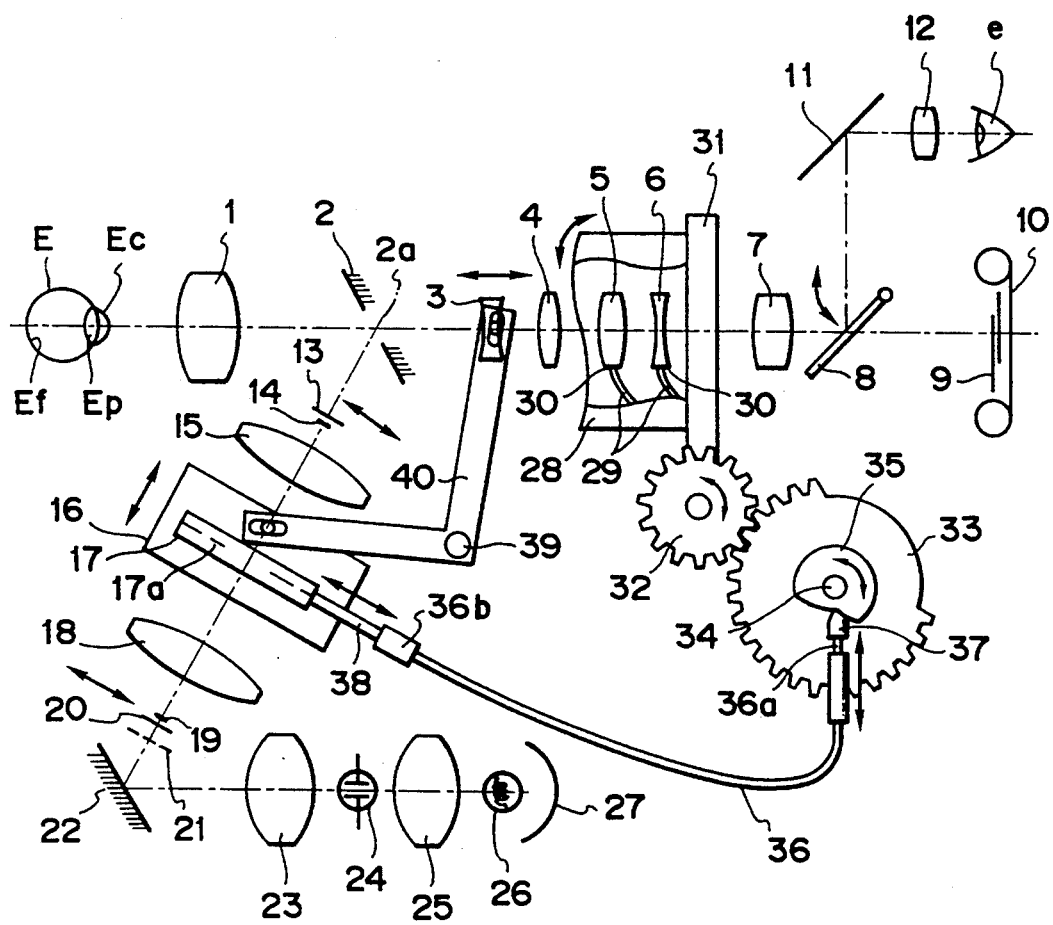
FIG. 1 shows the construction of a first embodiment of the present invention.

The present invention will hereinafter be described in detail with respect to some embodiments thereof shown in the drawings.

Referring to FIG. 1 which shows the construction of a first embodiment, an objective lens 1, an apertured mirror 2 formed with an opening 2a and for dividing photographing light and illuminating light, a focusing lens 3, a fixed lens 4, magnification change lenses 5 and 6 movable for a magnification change, a relay lens 7, a quick return mirror 8 adapted to be retracted out of the optical path as required, a shutter 9 and photographing film 10 are successively disposed in the direction of the visual axis of an eye E to be examined. An optical path changing mirror 11 and an eyepiece 12 are disposed in the direction of reflection of the quick return mirror 8 so that a finder light beam may be directed to an examining eye e. The members from the objective lens 1 to the photographing film 10 together constitute a photo-taking optical system, in which the members from the focusing lens 3 to the magnification change lens 6 together constitute a magnification change imaging system.

Cornea baffles 13 and 14 each comprising a circular light intercepting plate for intercepting harmful reflected light from a cornea Ec, a relay lens 15, an illuminating field stop 17 fixed to a movable plate 16 and capable of changing the diameter of its opening, a relay lens 18, and crystalline lens baffles 19 and 20 each comprising a circular light intercepting plate for preventing harmful reflected light from a crystalline lens Ep, a ring slit 21 having an opening at the center thereof, an optical path changing mirror 22, a first condensing lens 23, a light source 24 for photographing comprising a stroboscopic tube, a second condensing lens 25, a light source 26 for observation comprising an incandescent lamp, and a condensing mirror 27 are disposed in the incidence direction of the apertured mirror 2.

The apertured mirror 2 is disposed at the point of intersection between the optical axis of the photo-taking optical system and an optical system linking the relay lenses 15 and 18 together, and with respect to this apertured mirror 2, the cornea baffles 13 and 14 are disposed conjugately with the front face of the cornea Ec, the crystalline lens baffles 19 and 20 are disposed conjugately with the rear face of the crystalline lens, and the ring slit 21 is disposed conjugately with the pupil Ep. Also, the movable plate 16 is guided by a guide mechanism, not shown, and is movable in the direction of the optical axis of the illuminating optical system as indicated by the illustrated arrow.

On the other hand, the magnification change lenses 5 and 6 of the magnification change imaging system are engaged with cam slots 29 and 29 formed in a cam ring 28, through pins 30 and 30, which in turn are engaged with a straight cam, not shown. A first gear 31 is secured to the cam ring 28 and is connected to a partly untoothed third gear 33 through a second gear 32. Thus, the cam ring 28 follows the rotation of the third gear 33 and the magnification change lenses 5 and 6 are moved in the direction of the optical axis thereof, whereby the field angle is changed from a wide field angle to a narrow field angle. The third gear 33 is mounted on a magnification change shaft 34 connected to a magnification change knob, not shown, or a power source for magnification change, not shown, and a peripheral surface cam plate 35 is fixed to the magnification change shaft 34. The peripheral surface cam plate 35 is rotated in response to the magnification changing operation, and the amount of displacement thereof acts to harmonize the field angle of the photo-taking optical system, i.e., the photographing range of the eye fundus Ef, and the range in which illuminating light is intercepted by the illuminating field stop 17.

That is, the peripheral surface cam plate 35 and the illuminating field stop 17 is are connected together by a release cable 36a which slides in the interior of a drive cord 36. The drive cord 36 and the release cable 36a have flexibility like a drive cord for operating the shutter button of a camera, and a contact 37 and a connecting pin 38 are interposed between the opposite ends thereof. Of the end portions 36a and 36b of the drive cord 36, the end portion 36b is fixed to the end edge of the movable plate 16, and the drive cord 36 is made non-retractile, that is, the opposite ends of the release cable 36a are made highly rigid, so that the amount of movement of the end portion 36a may be accurately transmitted to the end portion 36b.

Further, the focusing lens 3 is connected by a combination of a pin and a hole to one end of a focusing arm 40 fixed to a focusing shaft 39, and the movable plate 16 is likewise connected by a combination of a pin and a hole to the other end of the focusing arm 40. The focusing shaft 39 is coupled to a focusing knob, not shown, and by turning the focusing knob, the focusing lens 3 may be moved in the direction of the optical axis. The focusing of the photo-taking optical system can also be accomplished by changing the length of the optical path between the relay lens 7 and the photographing film 10, and the focusing of the magnification change imaging system can also be accomplished by mounting a zoom lens and lenses of different focal lengths in the fashion of a turret.

Figure 2:
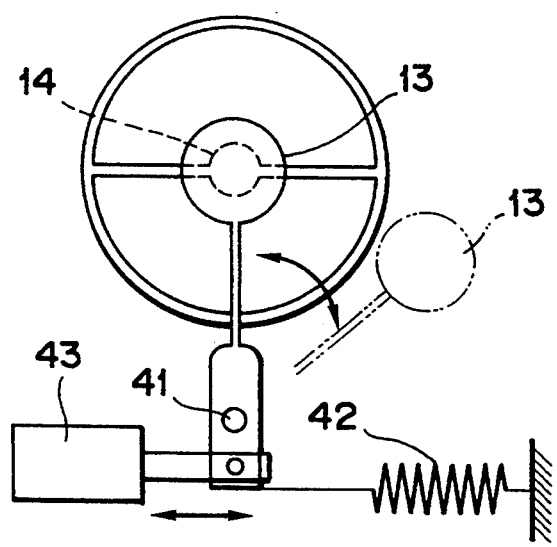
FIG. 2 is a front view of a cornea baffle and a crystalline lens baffle.

FIG. 2 is a front view of the cornea baffles 13 and 14 as they are seen in the direction of the optical axis, and the cornea baffle 13 comprising a large-diametered light intercepting plate is superposed on the cornea baffle 14 comprising a small-diametered light intercepting plate, and the cornea baffle 13 is adapted to rotate about a shaft 41. Usually, the cornea baffle 13 is pulled by a tension spring 42 and is located on the cornea baffle 14, but can always be retracted out of the optical path by a solenoid 43 being operated. The crystalline baffles 19 and 20 are similar in construction to the cornea baffles 13 and 14, and the cornea baffles 13 and 14 may assume, besides such a construction, for example, a construction in which large and small black spots are provided on a transparent glass plate and they are changed over, or a construction in which light intercepting areas of various sizes and shapes are formed on a liquid crystal plate.

In such a construction, a light beam emitted from the light source 26 for observation passes through the second condensing lens 25 and the first condensing lens 23, is reflected by the optical path changing mirror 22, and is converged on and illuminates the ring slit 21. The opening in the illuminated ring slit 21 becomes an annular secondary light source and emits a light beam, which is converged by the relay lenses 18 and 15 and forms a secondary light source image on the apertured mirror 2. The light beam further reflected by the apertured mirror 2 forms a secondary light source image on the pupil Ep by the objective lens 1 and uniformly illuminates the eye fundus Ef over a wide range. Scattered reflection occurs on the illuminated eye fundus Ef, and some reflected light passing through the opening 2a in the apertured mirror 2 passes through the central area of the secondary light source image, i.e., that portion of the ring slit 21 which corresponds to the image of the light intercepting area, and emerges from the eye E to be examined and enters the objective lens 1 and once forms an intermediate image there. Subsequently, this reflected light passes through the opening 2a in the apertured mirror 2 and enters the magnification change imaging system, and is converged there and is reflected by the quick return mirror 8, and passes through the direction changing mirror 11 and the eyepiece 21 and thus, the image of the eye fundus can be observed by the examining eye e.

The illuminating field stop 17 comprising an iris diaphragm and having a variable opening covers a portion to which the illuminating light is applied with the image of the stop except for the photographed range of the eye fundus Ef, and prevents harmful light from mixing with the photographing light. Accordingly, the location of this illuminating field stop 17 must be conjugate with the eye fundus Ef irrespective of the visibility of the eye E to be examined and at the same time, the stop vane 17a of the illuminating field stop 17 is required to be opened and closed corresponding to the field angle of the photo-taking optical system. Also, the illuminating field stop 17 is required to be interlocked with the focusing lens 3 by the focusing arm 40 so that when the focusing lens 3 is moved and the focus of the photo-taking optical system is adjusted with respect to the eye fundus Ef, the illuminating field stop 17 may become conjugate with the eye fundus Ef with respect to the relay lens 15, the apertured mirror 2 and the objective lens 1.

Figure 3:
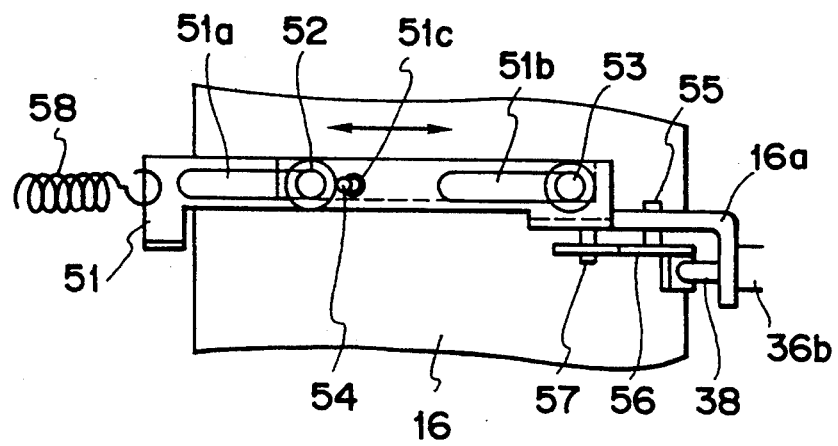
FIG. 3 is a plan view of an illuminating field stop.
Figure 4:
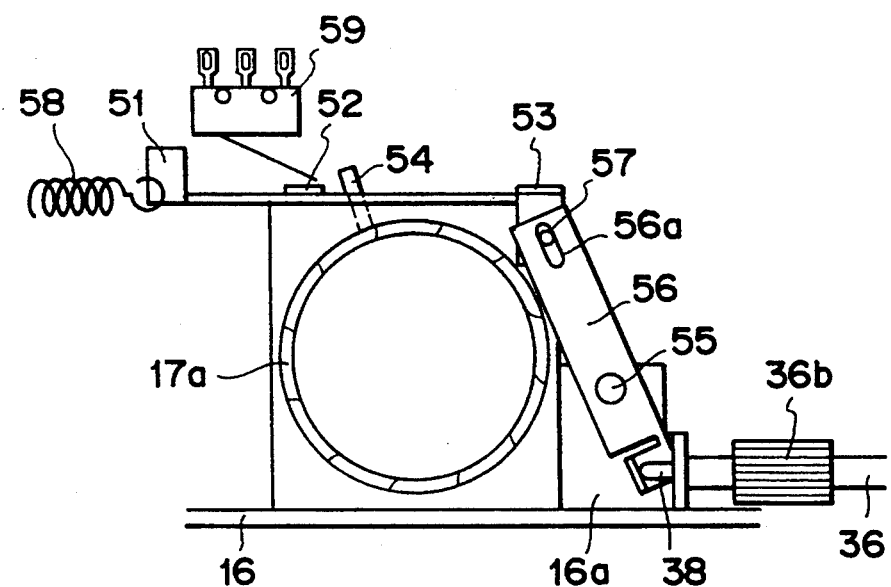
FIG. 4 is a front view showing the state of the illuminating field stop corresponding to a wide field angle.
Figure 5:
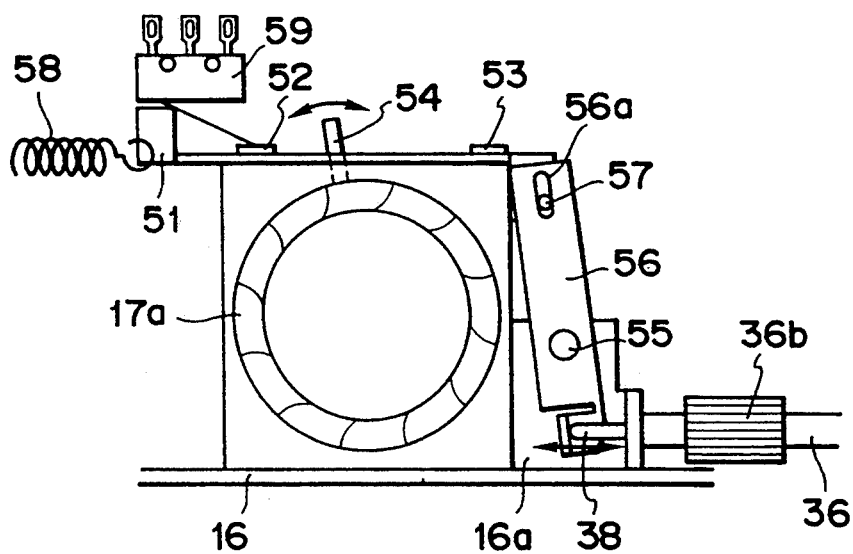
FIG. 5 is a front view showing the state of the illuminating field stop corresponding to a narrow field angle.
Figure 6:
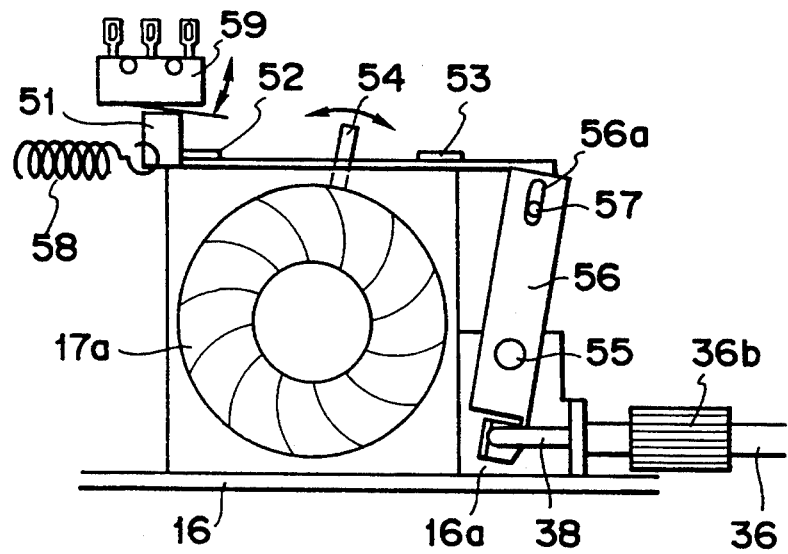
FIG. 6 is a front view showing the state of the illuminating field stop corresponding to a small pupil diameter.

FIG. 3 is a plan view of such an illuminating field stop 17, FIG. 4 is a front view showing a state in which the stop vane 17a is opened corresponding to a wide field angle, FIG. 5 is a front view showing a state in which the stop vane 17a is closed correspondingly to the narrowest field angle, and FIG. 6 is a front view showing a state in which the stop vane 17a is closed corresponding to a small pupil diameter. A sliding plate 51 is formed with guide slots 51a, 51b and a hole 51c, and guide screws 52 and 53 are threadably engaged with a support member for the stop vane 17a. The slots 51a and 51b are loosely fitted over the guide screws 52 and 53, respectively, so that the sliding plate 51 may be movable in a direction perpendicular to the optical axis. Accordingly, during a magnification change, the illuminating field stop 17 is not displaced in the direction of the optical axis and the in-focus state is not spoiled.

An opening-closing pin 54 is fitted in the hole 51c of the sliding plate 51, and when the sliding plate 51 is moved, the stop vane 17a is opened and closed. A shaft 55 is studded in the rising portion 16a of the movable plate 16, and a lever 56 is rotatably supported on the shaft 55. Further, a slot 56a is formed in one end portion of the lever 56, and a pin 57 studded in the bent portion of the sliding plate 51 is fitted in the slot 56a. The other end of the lever 56 is bent and bears against the connecting pin 38. A tension coil 58 is mounted between the sliding plate 51 and a portion of the movable plate 16 so that the lever 56 may normally be biased counter-clockwise. A detection switch 59 is provided for detecting the movement of the sliding plate 51.

When as shown in FIG. 1, for the purpose of focusing, the examiner looks into the eyepiece 12 and observes the eye fundus Ef and turns a focusing knob, not shown, to thereby rotate the focusing shaft 39, the focusing lever 40 is rotated and the focusing lens 3 is moved. At a point of time at which an in-focus state is obtained, the focusing operation is stopped and the focusing lens 3 is stopped in that position. In that case, the movable plate 16 is also interlocked by the rotation of the focusing lever 40 and the illuminating field stop 17 assumes a position conjugate with the eye fundus Ef. On the other hand, when for the purpose of a magnification change, the examiner turns a magnification change knob, not shown, to thereby rotate the magnification change shaft 34, the magnification change lenses 5 and 6 follow the third gear 33, the second gear 32 and the first gear 31, whereby the angle of field is varied. At the same time, the peripheral surface cam plate 35 is also rotated to vertically move the contact 37, and the release cable 36a follows as indicated by arrow to thereby move the connecting pin 38 to the right and left.

At this time, as shown in FIGS. 4 to 6, the lever 56 is rotated in response to the movement of the connecting pin 38 and the sliding plate 51 follows it and the opening-closing pin 54 is moved, whereby the stop vane 17a is stopped down or opened. For example, when the photo-taking optical system is set to a wide field angle, i.e., a short focal length, the stop vane 17a is opened as shown in FIG. 4 and the entire photographing range on the eye fundus Ef is illuminated by the illuminating optical system. Also, when the photo-taking optical system is set to a narrow field angle, i.e., a long focal length, the stop vane 17a is stopped down as shown in FIG. 5, and the portion around the photographing range on the eye fundus Ef is covered with the shadow of the stop. When the eye E to be examined having a small pupil diameter is to be photographed from the narrow field angle, the cornea baffle 13 and the crystalline lens baffle 20 are each changed over to a small-diametered light intercepting plate to make up for the deficiency in the quantity of light and at the same time, the stop vane 17a is stopped down as shown in FIG. 6 because flare or the like becomes liable to occur. Also, where as previously described, the lenses are mounted in the fashion of a turret, the variation in the field angle also becomes discontinuous and therefore, the opening-closing of the stop becomes discontinuous.

Figure 7:
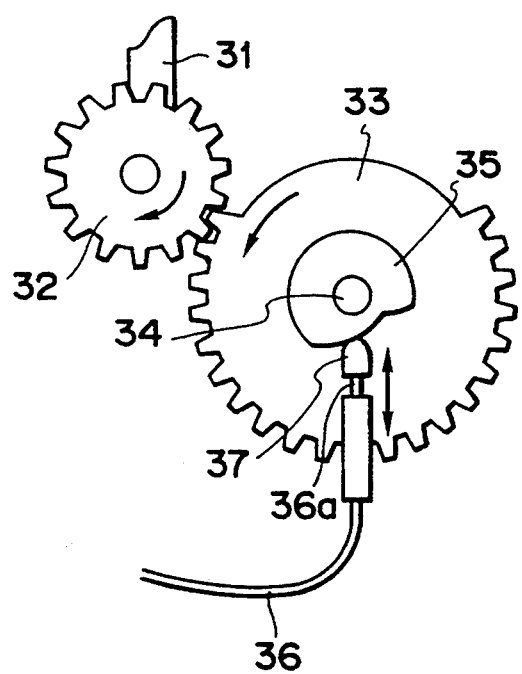
FIG. 7 shows the forms of gears and a peripheral surface cam plate for a magnification change.
Figure 8:
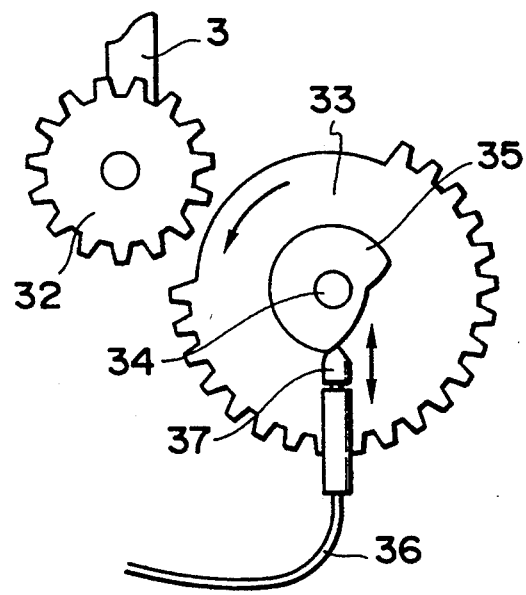
FIG. 8 shows the forms of the gears and peripheral surface cam plate for a magnification change.

FIG. 7 shows the state of the gears for a magnification change during the minimum view angle, i.e., during the maximum magnification. When as shown in FIG. 8, the third gear 33 is rotated counter-clockwise and the second gear 32 is rotated, the meshing engagement between the third gear 33 and the second gear 32 is released during the minimum field angle because the third gear 33 is a partially untoothed gear. When from this state, a magnification change knob, not shown, is turned to further rotate the magnification change gear 34 counter-clockwise, the third gear 33 comes out of meshing engagement with the second gear 32 and thus, no longer affects the magnification change.

However, the peripheral surface cam plate 35 fixed to the magnification change shaft 34 is rotated counter-clockwise to thereby depress the contact 37, and the connecting pin 38 is protrudes through the release cable 36a. By such a series of operations, as shown in FIG. 6, the sliding plate 51 is further moved rightwardly to thereby move the opening-closing pin 54 and further stop down the stop vane 17a and at the same time, a portion of the sliding plate 51 actuates the detection switch 59. The signal from the detection switch 59 moves the cornea baffle 13 and the crystalline lens baffle 20 out of the optical path and changes over them to the small-diametered light intercepting plate, thus bringing about a state in which the eye E to be examined having a small pupil diameter is photographed. In this manner, the magnification change knob, not shown, is turned so as to change the magnification from a low magnification to a high magnification whereafter the knob is further rotated in the same direction, whereupon the illuminating field stop comes to be stopped down with the magnification remaining unchanged.

Figure 9:
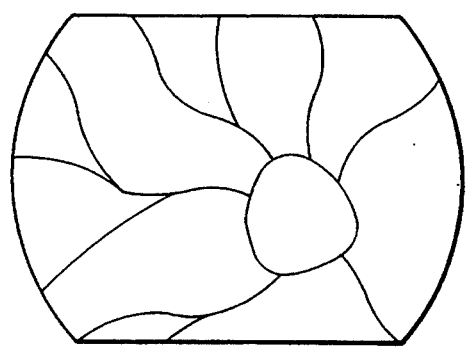
FIG. 9 is a schematic view of the image of the eye fundus corresponding to a narrow field angle.
Figure 10:
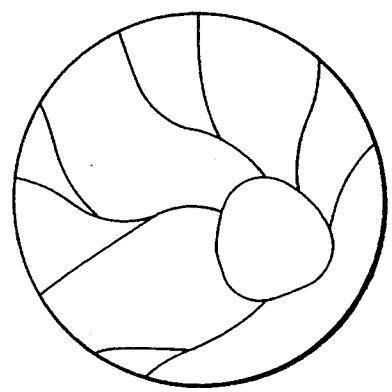
FIG. 10 is a schematic view of the image of the eye fundus corresponding to a small pupil diameter.

FIG. 9 is a schematic view of an image obtained when photographing is effected at the ordinary narrow field angle, and FIG. 10 is a schematic view of an image obtained when the eye E to be examined having a small pupil diameter is photographed. To return the photographing field angle to the ordinary photographing state, the magnification change knob, not shown, can be turned to thereby rotate the magnification change shaft 34 clockwise and rotate the peripheral surface cam plate 35, thus opening the illuminating field stop 17 and also bringing the third gear 33 and the second gear 32 into meshing engagement with each other.

Figure 11:
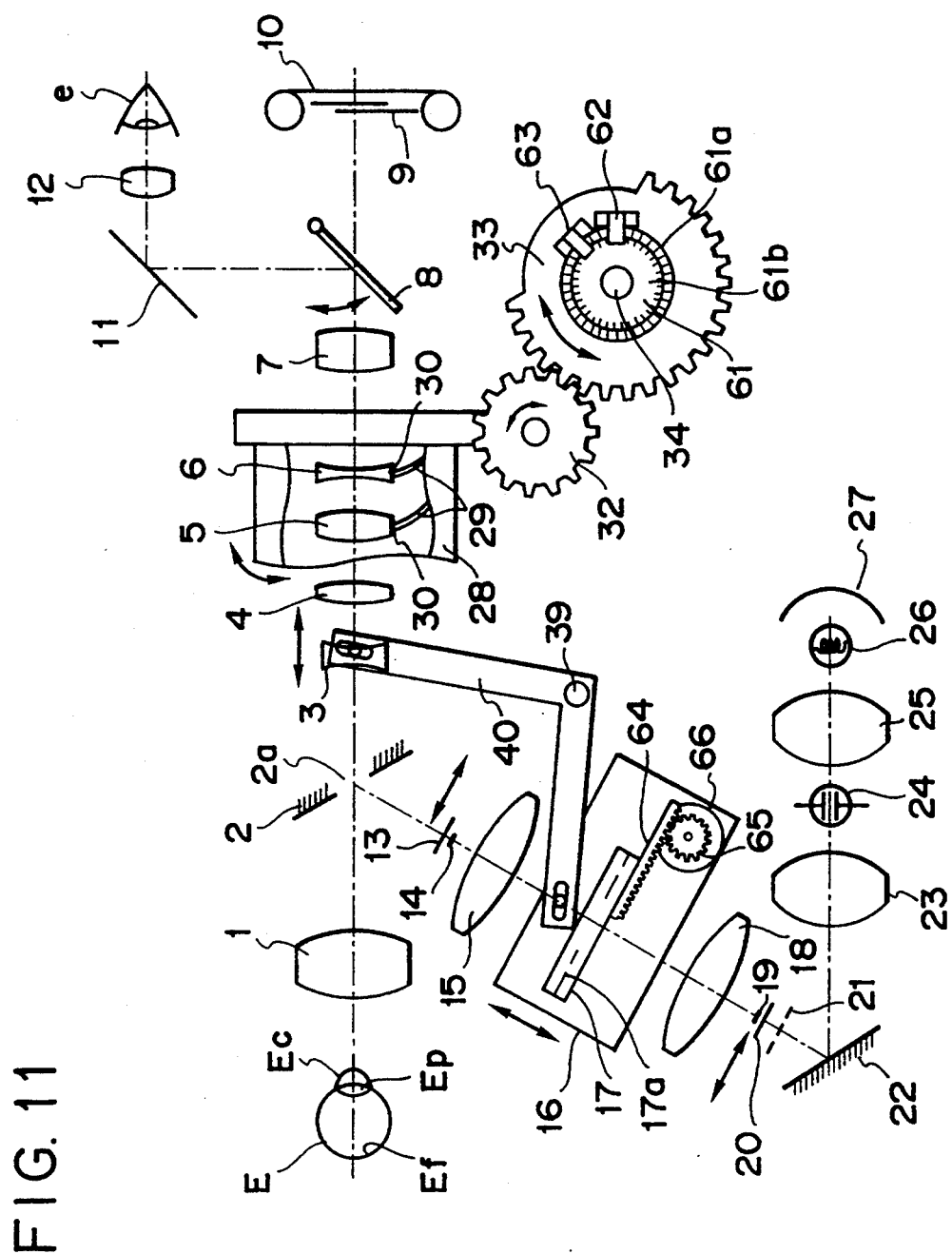
FIG. 11 shows the construction of a second embodiment of the present invention.
Figure 12:
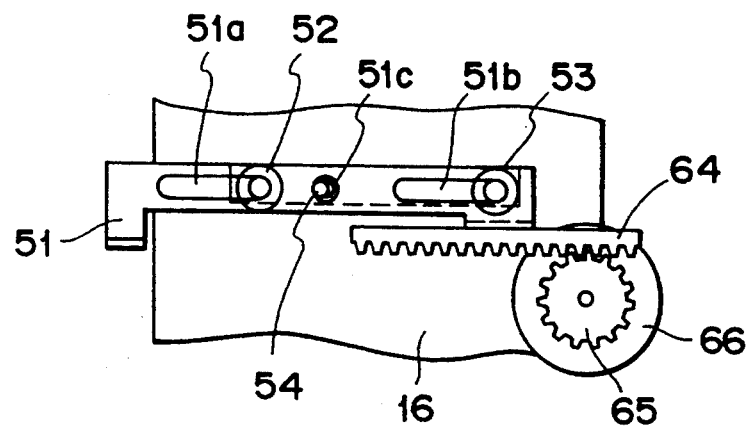
FIG. 12 is a plan view of the illuminating field stop.

FIG. 11 shows the construction of a second embodiment, and FIG. 12 is a fragmentary enlarged plan view of the illuminating field stop 17. In the present embodiment, the third gear 33 and the illustrating field stop 17, instead of the release cable 36a in the first embodiment, are electrically connected together. That is, a slit disc 61, instead of the peripheral surface cam plate 35, is mounted on the magnification change shaft 34, and outer slits 61a and inner slits 61b which are ½ out of phase with each other are provided in the slit disc 61. Optical sensors 62 and 63 are fixed to an eye fundus camera body by a member, not shown, so as to detect one of the slit 61a and the slit 61b. A rack gear 64 is fixed to the sliding plate 51 adjacent to the illuminating field stop 17, and is connected to a stepping motor 66 through a pinion gear 65.

By such a construction, the angle of rotation is calculated from the number of the slits 61a and 61b which have passed the optical sensors 62 and 63, and the direction of rotation is calculated from the phase difference between the two optical sensors 62 and 63, whereby the angle of rotation of the third gear 33, i.e., the photographing field angle, is detected. The rotation of the stepping motor 66 is controlled on the basis of this detected signal, and the rotation of the pinion gear 65 is transmitted to the sliding plate 51 through the rack gear 64. The sliding plate 51 opens and closes the stop vane 17a and thus, as in the first embodiment, it becomes able to cope with a case where the eye E to be examined having a small pupil diameter is photographed.

The slit disc 61 may be replaced by a potentiometer utilizing electrical resistance. Also, instead of only the illuminating field stop 17 being moved by the detection signal, the cornea baffles 13, 14 and the crystalline lens baffles 19, 20 may also be moved at a time.

What is claimed is:

1. An eye fundus photographing apparatus comprising:
    an optical system comprising means for illuminating the fundus of an eye to be examined and means for causing the fundus of the eye to be examined to be photographed with different photographing magnifications;
    an operating mechanism comprising means for changing the photographing magnification, by operating in a predetermined manner; and
    interlocking means for varying a portion of said optical system without changing the photographing magnification, by performing an operation with said operating mechanism following the operation performed by said operating mechanism in the predetermined manner for changing the photographing magnification by said optical system.

2. An apparatus according to claim 1, wherein said interlocking means varies the inner diameter of an illuminating field stop in said optical system.

3. An apparatus according to claim 1, wherein said interlocking means varies a portion of said optical system also when the photographing magnification of said optical system is changed.

4. An apparatus according to claim 1, wherein said interlocking means mechanically transmits the operation of said operating mechanism to a portion of said optical system to thereby vary the portion of said optical system.

5. An apparatus according to claim 1, wherein said interlocking means photoelectrically detects the operation performed by said operating mechanism and varies a portion of said optical system on the basis of said detection.

6. An apparatus according to claim 1, wherein said interlocking means has a partly untoothed gear, and varies a portion of said optical system without changing said photographing magnification, by the action of said gear.

7. An eye fundus camera comprising:
    a photographing system comprising means for photographing the fundus of an eye to be examined at different photographing magnifications;
    magnification changing means for changing the photographing magnification, the photographing magnification of said photographing system being changed by a predetermined operation performed by said magnification changing means;
    an illuminating field stop comprising means for limiting the illuminated range of the fundus of the eye to be examined; and
    interlocking means for varying the inner diameter of said illuminating field stop without changing said photographing magnification, by performing an operation following the predetermined operation performed by said magnification changing means for changing the photographing magnification of said photographing system from a low magnification to a high magnification.

8. A camera according to claim 7, further comprising an illuminating system for the illumination of the fundus of the eye to be examined having said illuminating field stop disposed in the optical path thereof,
    and light intercepting means of a variable size or position disposed at a location in the optical path of said illuminating system which is substantially conjugate with the front eye part of the eye to be examined, wherein said interlocking means varies the size or position of said light intercepting means by an operation following the operation performed by said magnification changing means for changing the photographing magnification of said photographing system from a low magnification to a high magnification.

9. A camera according to claim 7, wherein said illuminating field stop varies its inner diameter in operative association with the change of the photographing magnification of said photographing system 10. A camera according to claim 7, wherein said interlocking means has a partly untoothed gear, and varies the inner diameter of said illuminating field stop without changing said photographing magnification, by the action of said gear.

11. An eye fundus photographing apparatus comprising:
    an optical system comprising means for illuminating the fundus of an eye to be examined and means for causing the fundus of the eye to be examined to be photographed with different photographing magnifications;
    operating means for changing the photographing magnification by operating in a predetermined manner; and
    interlocking means for, in a non-interlocked state, varying a portion of said optical system without changing the photographing magnification by performing an operation with said operating means following the operation performed by said operating means in the predetermined manner and for, in an interlocked state, changing the photographing magnification by performing an operation with said operating mechanism following the operating of the operating mechanism in the predetermined manner.

* * * * *

UNITED STATES PATENT AND TRADEMARK OFFICE
CERTIFICATE OF CORRECTION

PATENT NO. : 5,446,509
DATED : August 29, 1995
INVENTOR(S) : SATORU OKINISHI

It is certified that error appears in the above-indentified patent and that said Letters Patent is hereby corrected as shown below:

COLUMN 2

Line 21, "for" should read --for performing a--.

COLUMN 4

Line 48, "correspondingly" should read --corresponding--.

COLUMN 5

Line 12, "of" should read --in--.
    Line 23, "angle of field" should read --field angle--.

COLUMN 8

Line 25, "system" should read --system.--.

Signed and Sealed this

Nineteenth Day of December, 1995

Attest:

BRUCE LEHMAN

*Attesting Officer*        *Commissioner of Patents and Trademarks*